(12) United States Patent
Inoue et al.

(10) Patent No.: US 7,713,341 B2
(45) Date of Patent: May 11, 2010

(54) QUATERNARY AMMONIUM SALT COMPOSITIONS

(75) Inventors: Katsuhisa Inoue, Wakayama (JP);
Hidehito Ikebata, Wakayama (JP);
Kazuhiko Kurita, Wakayama (JP);
Tetsuaki Fukushima, Wakayama (JP);
Tadayuki Suzuki, Wakayama (JP)

(73) Assignee: Kao Corporation, Tokyo (JP)

( * ) Notice: Subject to any disclaimer, the term of this patent is extended or adjusted under 35 U.S.C. 154(b) by 232 days.

(21) Appl. No.: 12/078,690

(22) Filed: Apr. 3, 2008

(65) Prior Publication Data

US 2009/0293763 A1 Dec. 3, 2009

(30) Foreign Application Priority Data

Apr. 10, 2007 (JP) .............................. 2007-102708

(51) Int. Cl.
*A01N 33/12* (2006.01)
*A01N 33/02* (2006.01)
*B27K 3/34* (2006.01)
*B27K 3/50* (2006.01)
*B27K 3/00* (2006.01)

(52) U.S. Cl. .................. 106/18.32; 106/18.35; 514/506; 514/642; 564/281; 564/291; 564/296

(58) Field of Classification Search .............. 106/18.32, 106/18.35; 514/506, 642; 564/281, 291, 564/296
See application file for complete search history.

(56) References Cited

U.S. PATENT DOCUMENTS

| | | | | |
|---|---|---|---|---|
| 4,871,473 | A | * | 10/1989 | Goettsche et al. ......... 427/427.6 |
| 4,970,201 | A | * | 11/1990 | Giebeler et al. ............... 514/64 |
| 5,186,947 | A | * | 2/1993 | Goettsche et al. ........... 424/638 |
| 6,211,218 | B1 | * | 4/2001 | Goettsche et al. ........... 514/383 |
| 2003/0010956 | A1 | * | 1/2003 | Las et al. .................... 252/380 |
| 2006/0251915 | A1 | * | 11/2006 | Jin et al. ...................... 428/541 |
| 2007/0151476 | A1 | * | 7/2007 | Humar et al. .................. 106/12 |
| 2007/0207076 | A1 | * | 9/2007 | Guzzetta et al. ............... 423/27 |
| 2007/0254109 | A1 | * | 11/2007 | Sauer et al. .................. 427/420 |
| 2007/0260089 | A1 | * | 11/2007 | Sauer et al. .................. 564/281 |
| 2009/0211487 | A1 | * | 8/2009 | Grady et al. ............. 106/18.32 |

FOREIGN PATENT DOCUMENTS

| | | | |
|---|---|---|---|
| EP | 0238413 A1 | * | 9/1987 |
| JP | 2000-336070 A | * | 12/2000 |
| WO | WO2007/005195 A1 | * | 1/2007 |

OTHER PUBLICATIONS

Derwent Acc-No. 2002-554823, abstract of Korean Patent Specification No. 2001-112779A (Jun. 2000).*

* cited by examiner

*Primary Examiner*—Anthony J Green
(74) *Attorney, Agent, or Firm*—Birch, Stewart, Kolasch & Birch, LLP

(57) ABSTRACT

The present invention relates to a quaternary ammonium salt composition containing (a) a quaternary ammonium salt represented by the following general formula (1), (b) a specific tertiary amine and (c) an organic acid ester in specific mass ratios which is excellent in hue and storage stability, a process for producing the quaternary ammonium salt composition, and a wood preservative containing the quaternary ammonium salt composition.

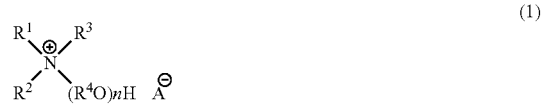

(1)

wherein $R^1$ is an alkyl or alkenyl group; $R^2$ is an alkyl, alkenyl or hydroxyalkyl group; $R^3$ is an alkyl or hydroxyalkyl group; $R^4$ is an alkylene group; n is a number of from 1 to 5; and A is a counter ion derived from sulfonic acid, etc.

6 Claims, No Drawings

QUATERNARY AMMONIUM SALT COMPOSITIONS

FIELD OF THE INVENTION

The present invention relates to quaternary ammonium salt compositions having excellent hue and storage stability, a process for producing the quaternary ammonium salt compositions, and wood preservatives containing the quaternary ammonium salt compositions.

BACKGROUND OF THE INVENTION

Wood preservatives serve for protecting wood from damages by vermin or injurious insects such as termite, and quaternary ammonium salts having a high insect- or ant-proof capability and a high antiseptic or mildew-proof capability are known as the wood preservatives.

The quaternary ammonium salts are usually produced by quaternarizing tertiary amines. However, in many cases, since alkyl halides such as methyl chloride and methyl bromide are used as a quaternarizing agent, halogen ions such as chlorine ion and bromine ion tend to be inevitably included in the obtained quaternary ammonium salts. As a result, when the halogens contained in the quaternary ammonium salts are contacted with metals, rusts tend to be generated, thereby causing problems such as damage to production apparatuses and, therefore, poor production efficiency. To solve the problems, organic acids have been used instead of the alkyl halides.

As the method for producing the quaternary ammonium salts using the organic acids, there are known an ion exchange resin method and an electrodialysis. However, in the ion exchange resin method, the ion-exchanged resin used must be subjected to an alkali treatment or an acid treatment for regenerating the resin, or the ion exchange resin must be periodically replaced with new one, resulting in prolonged production process, high costs for facilities and high production costs. Also, since the reaction used in the ion exchange resin method cannot be conducted at a high concentration, the ion exchange resin method is unsuitable for mass production of the quaternary ammonium salts. On the other hand, in the electrodialysis, only limited solvents are usable therein because of possibility of explosion upon using inflammable solvents, resulting in poor flexibility of the method.

Further, JP 2000-336070A discloses a method for synthesizing a quaternary ammonium salt by reacting a tertiary amine with an alkyl halide and then adding an alcohol containing sodium, etc., and an organic acid to the obtained reaction product for replacement of a counter ion of the salt. However, in this method, since a large amount of the solvent must be used in the reaction, the productivity tends to be lowered, and additional operations for removal or recovery of the solvent are also required. For this reason, in the above method, there tend to occur problems such as increase in size of production facilities, complicated production process and high production costs.

JP 4-57661B, JP 6-96243B and FUJIMOTO, Takehiko, "NEW INTRODUCTION TO SURFACE ACTIVE AGENTS", Sanyo Chemical Industries, Ltd., 1st Edition, Oct. 1, 1981, p. 68, disclose a method for producing a quaternary ammonium salt from a tertiary amine and an alkyleneoxide.

However, these conventional methods have problems such as low reaction rate, poor hue of the resultant products, deterioration in pH or hue upon storage.

SUMMARY OF THE INVENTION

The present invention relates to a quaternary ammonium salt composition including (a) a quaternary ammonium salt represented by the following general formula (1), (b) a tertiary amine represented by the following general formula (2), and (c) an organic acid ester represented by the following general formula (3), wherein a mass ratio of the component (a) to the component (b) [component (a)/component (b)] is from 100/0.01 to 100/7, and a mass ratio of the component (a) to the component (c) [component (a)/component (c)] is from 100/0.01 to 100/10; a process for producing the quaternary ammonium salt composition; and a wood preservative containing the quaternary ammonium salt composition.

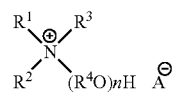
(1)

wherein $R^1$ is an alkyl or alkenyl group having 6 to 24 carbon atoms; $R^2$ is an alkyl, alkenyl or hydroxyalkyl group having 1 to 24 carbon atoms; $R^3$ is an alkyl or hydroxyalkyl group having 1 to 3 carbon atoms; $R^4$ is an alkylene group having 2 to 3 carbon atoms; n is an average molar number of addition of $R^4O$ groups ranging from 1 to 5; and A is a counter ion derived from an organic acid selected from the group consisting of sulfonic acid, a phosphate and a carboxylic acid;

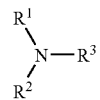
(2)

wherein $R^1$, $R^2$ and $R^3$ have the same meanings as defined above; and $$A\text{-}(R^4O)_mH \quad (3)$$

wherein $R^4$ and A have the same meanings as defined above; and m is an average molar number of addition of $R^4O$ groups ranging from 1 to 5;

DETAILED DESCRIPTION OF THE INVENTION

The present invention relates to a quaternary ammonium salt composition having excellent hue and storage stability, a process for producing the quaternary ammonium salt composition; and a wood preservative containing the quaternary ammonium salt composition.

The present inventors have found that the quaternary ammonium salt composition containing the quaternary ammonium salt, the tertiary amine and the organic acid ester in specific mass ratios is excellent in hue and storage stability.

Thus, the present invention relates to the following aspects [1] to [3]:

[1] A quaternary ammonium salt composition including (a) a quaternary ammonium salt represented by the following general formula (1), (b) a tertiary amine represented by the following general formula (2), and (c) an organic acid ester represented by the following general formula (3), wherein a mass ratio of the component (a) to the component (b) [component (a)/component (b)] is from 100/0.01 to 100/7, and a mass ratio of the component (a) to the component (c) [component (a)/component (c)] is from 100/0.01 to 100/10,

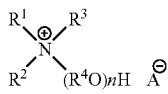  (1)

wherein $R^1$ is an alkyl or alkenyl group having 6 to 24 carbon atoms; $R^2$ is an alkyl, alkenyl or hydroxyalkyl group having 1 to 24 carbon atoms; $R^3$ is an alkyl or hydroxyalkyl group having 1 to 3 carbon atoms; $R^4$ is an alkylene group having 2 to 3 carbon atoms; n is an average molar number of addition of $R^4O$ groups ranging from 1 to 5; and A is a counter ion derived from an organic acid selected from the group consisting of sulfonic acid, a phosphate and a carboxylic acid;

  (2)

wherein $R^1$, $R^2$ and $R^3$ have the same meanings as defined above; and

A-(R$^4$O)$_m$H   (3)

wherein $R^4$ and A have the same meanings as defined above; and m is an average molar number of addition of $R^4O$ groups ranging from 1 to 5;

[2] a process for producing the quaternary ammonium salt composition as defined in the above aspect [1] from the tertiary amine (b), which includes the step of reacting the tertiary amine (b) with an alkyleneoxide (e) in the presence of water and an organic acid (d) at a temperature of from 30 to 90° C. wherein the water is present in an amount of from 0.5 to 30% by mass on the basis of the whole components charged, the organic acid (d) is present in an amount of from 0.95 to 1.5 mol per 1 mol of the tertiary amine (b), and the alkyleneoxide (e) is present in an amount of from 1.5 to 5.0 mol per 1 mol of the tertiary amine (b); and

[3] a wood preservative containing the quaternary ammonium salt composition as defined in the above aspect [1].

The quaternary ammonium salt composition of the present invention is characterized by containing the quaternary ammonium salt (a) represented by the following general formula (1), the tertiary amine (b) represented by the following general formula (2), and the organic acid ester (c) represented by the following general formula (3), wherein a mass ratio of the component (a) to the component (b) [component (a)/component (b)] is from 100/0.01 to 100/7, and a mass ratio of the component (a) to the component (c) [component (a)/component (c)] is from 100/0.01 to 100/10.

<Quaternary Ammonium Salt (a)>

The component (a) used in the present invention is a quaternary ammonium salt represented by the following general formula (1):

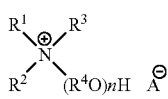  (1)

In the general formula (1), $R^1$ is a linear or branched alkyl or alkenyl group having 6 to 24 carbon atoms, preferably a linear alkyl group having 8 to 22 carbon atoms, more preferably a linear alkyl group having 8 to 18 carbon atoms, and still more preferably a linear alkyl group having 8 to 12 carbon atoms.

$R^2$ is a linear or branched alkyl, alkenyl or hydroxyalkyl group having 1 to 24 carbon atoms, preferably a methyl group or a linear or branched hydroxyalkyl group having 2 to 3 carbon atoms, or a linear alkyl group having 8 to 22 carbon atoms, more preferably a methyl group or a linear alkyl group having 8 to 18 carbon atoms, and still more preferably a linear alkyl group having 8 to 12 carbon atoms.

Specific examples of $R^1$ and $R^2$ include octyl, decyl, dodecyl, tetradecyl, hexadecyl and octadecyl. Among these groups, especially preferred is decyl.

$R^3$ is a linear or branched alkyl or hydroxyalkyl group having 1 to 3 carbon atoms, preferably an alkyl group having 1 to 2 carbon atoms, and more preferably a methyl group.

$R^4$ is a linear or branched alkylene group having 2 to 3 carbon atoms, and preferably an ethylene group. In addition, the suffix n represents an average molar number of addition of $R^4O$ groups, and is a number of from 1 to 5, preferably from 1 to 2 and more preferably from 1 to 1.2.

A is a counter ion derived from an organic acid selected from the group consisting of sulfonic acid, a phosphate and a carboxylic acid.

The most suitable quaternary ammonium salt represented by the general formula (1) is such a compound in which $R^1$ is a linear alkyl group having 8 to 18 carbon atoms, $R^2$ is a methyl group or a linear alkyl group having 8 to 18 carbon atoms, $R^3$ is a methyl group, $R^4$ is an ethylene group and n is a number of from 1 to 1.2.

<Tertiary Amine (b)>

The component (b) used in the present invention is a tertiary amine represented by the following general formula (2):

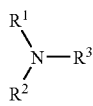  (2)

In the general formula (2), $R^1$, $R^2$ and $R^3$ have the same meanings as defined above.

Specific examples and preferred embodiments of $R^1$ to $R^3$ in the general formula (2) are the same as the specific examples and preferred embodiments of $R^1$ to $R^3$ in the general formula (1).

The most suitable tertiary amine represented by the general formula (2) is such a compound in which $R^1$ is a linear alkyl group having 8 to 18 carbon atoms, $R^2$ is a methyl group or a linear alkyl group having 8 to 18 carbon atoms, $R^3$ is a methyl group, $R^4$ is an ethylene group and n is a number of from 1 to 1.2.

Specific examples of the tertiary amine (b) include dimethyloctyl amine, dimethyldecyl amine, dimethyldodecyl amine, dimethyltetradecyl amine, dimethylhexadecyl amine, dimethyloctadecyl amine, dioctylmethyl amine, didecylmethyl amine, didodecylmethyl amine, ditetradecylmethyl amine, dihexadecylmethyl amine, dioctadecylmethyl amine, N-methyl-N-decyl-dodecyl amine, N-methyl-N-dodecyl-tetradecyl amine, N-methyl-N-tetradecyl-hexadecyl amine and N-methyl-N-hexadecyl-octadecyl amine. Among these tertiary amines, preferred are dimethylhexadecyl amine, dimethyloctadecyl amine, dioctylmethyl amine, didecylmethyl amine, didodecylmethyl amine and ditetradecylmethyl amine, and more preferred are dimethyloctadecyl amine, didecylmethyl amine and didodecylmethyl amine.

<Organic Acid Ester (c)>

The component (c) used in the present invention is an organic acid ester represented by the following general formula (3):

$$A\text{-}(R^4O)_mH \qquad (3)$$

In the general formula (3), $R^4$ and A have the same meanings as defined above; and m is an average molar number of addition of $R^4O$ groups ranging from 1 to 5. That is, A is a moiety (counter ion) derived from an organic acid selected from the group consisting of a sulfonic acid, a phosphate and a carboxylic acid. More specifically, A is preferably the organic acid described below as those used for producing the quaternary ammonium salt composition of the present invention. $R^4$ is preferably an ethylene group. Further, m is preferably a number of from 1 to 2 and more preferably from 1 to 1.2.

The most suitable organic acid ester represented by the general formula (3) is such a compound in which $R^1$ is a linear alkyl group having 8 to 18 carbon atoms; $R^2$ is a methyl group or a linear alkyl group having 8 to 18 carbon atoms; $R^3$ is a methyl group; $R^4$ is an ethylene group; and m is a number of from 1 to 1.2.

In the quaternary ammonium salt composition of the present invention, the mass ratio of the quaternary ammonium salt (a) to the tertiary amine (b) [component (a)/component (b)] is from 100/0.01 to 100/7, preferably from 100/0.01 to 100/5 and more preferably from 100/0.05 to 100/3, and the mass ratio of the quaternary ammonium salt (a) to the organic acid ester (c) [component (a)/component (c)] is from 100/0.01 to 100/10, preferably from 100/0.01 to 100/8 and more preferably from 100/0.05 to 100/6.

Further, in the quaternary ammonium salt composition of the present invention, the mass (content) of the quaternary ammonium salt (a) represented by the general formula (1) wherein n is 1 (n=1) is preferably from 93 to 100% by mass, more preferably from 95 to 100% by mass and still more preferably from 97 to 100% by mass on the basis of a total mass of the whole quaternary ammonium salts (a) contained in the composition.

The quaternary ammonium salt composition of the present invention is suitably produced by the method in which the tertiary amine (b) represented by the general formula (2) as a starting material is reacted with an alkyleneoxide (e) in the presence of water and an organic acid (d) at a temperature of preferably from 30 to 90° C. and especially preferably from 50 to 78° C. under such a condition that the water is preferably present in an amount of from 0.5 to 30% by mass and especially preferably from 1 to 10% by mass on the basis of a total amount of the whole components charged, the organic acid (d) is preferably present in an amount of from 0.95 to 1.5 mol and especially preferably from 1.01 to 1.25 mol per 1 mol of the tertiary amine (b), and the alkyleneoxide (e) is preferably present in an amount of from 1.5 to 5.0 mol and especially preferably from 1.7 to 3.0 mol per 1 mol of the tertiary amine (b).

The amount of water used in the present invention is preferably from 0.5 to 30% by mass, especially preferably from 0.8 to 15% by mass and still more preferably from 1 to 10% by mass on the basis of a total amount of the whole components charged, in particular, in view of enhanced productivity owing to a good reaction rate and a good reaction conversion rate.

Meanwhile, the "reaction conversion rate" used herein means a mole percentage (mol %) of the crude product to the tertiary amine (assuming that the crude product is composed of 100% of the quaternary ammonium salt; this is similarly applied to the following descriptions).

<Organic Acid (d)>

The organic acid (d) used in the present invention provides a counter ion $A^-$ of the quaternary ammonium salt (a) represented by the above general formula (1).

In the general formula (1), A is preferably a counter ion derived from a sulfonic acid or a carboxylic acid having 1 to 8 carbon atoms and more preferably a counter ion derived from a carboxylic acid having 1 to 5 carbon atoms.

Specific examples of the organic acid include acetic acid, propionic acid, glycolic acid, gluconic acid, lactic acid, malic acid, tartaric acid, citric acid, maleic acid, malonic acid, p-toluenesulfonic acid and alkyl phosphoric acids. Among these organic acids, in view of improving a hue and a storage stability of the resultant composition, preferred are acetic acid, propionic acid, glycolic acid, gluconic acid and p-toluenesulfonic acid, and more preferred are acetic acid, propionic acid and glycolic acid.

The amount of the organic acid (d) used is preferably from 0.95 to 1.5 mol, more preferably from 1.0 to 1.4 mol and still more preferably from 1.01 to 1.25 mol per 1 mol of the tertiary amine (b) in view of a good reaction conversion rate as well as a good pH stability and a good hue stability upon storage.

<Alkyleneoxide (e)>

Examples of the suitable alkyleneoxide (e) include ethyleneoxide and propyleneoxide. Among these alkyleneoxides, preferred is ethyleneoxide.

The amount of the alkyleneoxide (e) used is preferably from 1.5 to 5.0 mol, more preferably from 1.6 to 4.0 mol and still more preferably from 1.7 to 3.0 mol per 1 mol of the tertiary amine (b) in view of a good reaction rate and a good reaction conversion rate.

<Reaction Conditions>

The reaction temperature is preferably from 30 to 90° C., more preferably from 40 to 85° C. and still more preferably from 50 to 78° C. in view of a good reaction conversion rate.

The reaction time varies depending upon the reaction temperature, and is preferably from 0.25 to 25 h, more preferably from 0.5 to 15 h and still more preferably from 1 to 10 h.

In the process of the present invention, the reaction may be conducted in the presence of a solvent.

The solvent usable in the reaction of the production process is not particularly limited. Specific examples of the solvent include methanol, ethanol, propanol, isopropanol, ethylene glycol, diethylene glycol, triethylene glycol, 1,2-propanediol, 1,3-propanediol, polyethylene glycol and glycerol. Among these solvents, preferred are ethylene glycol and diethylene glycol.

The amount of the solvent used in the reaction of the production process is preferably 75% by mass or less, more preferably 60% by mass or less and still more preferably 40% by mass or less on the basis of a total amount of the whole components charged in view of a good productivity.

In addition, in order to prevent deteriorated hue upon the reaction, an inert gas such as nitrogen may be used, if required. More specifically, an interior of the reaction system may be replaced with the inert gas, or the reaction may be conducted while flowing the inert gas therethrough.

The quaternary ammonium salt composition of the present invention may be applied to preservatives, sterilizers, antiseptic agents, agricultural chemical formulations, etc. Specific examples of the products to which the quaternary ammonium salt composition of the present invention is especially effectively applicable, include wood preservatives, sterilizers for livestock barns, promoters for enhancing efficiencies of animal fungicides and agricultural chemical formulations, etc.

<Wood Preservative>

The quaternary ammonium salt composition of the present invention is free from deterioration in hue and pH upon storage and, therefore, exhibits an excellent storage stability. For this reason, the quaternary ammonium salt composition is effectively used in the applications requiring a good storage stability, in particular, is useful as a raw material of wood preservatives.

The wood preservative used herein means a chemical agent for protecting a wood used in general industrial materials and civil engineering materials against damage by vermin or injurious insects of wood such as termite, or killing wood destroying fungi or mildews or suppressing growth thereof to prevent the wood from being rotted or deteriorated.

When using the quaternary ammonium salt composition of the present invention as a wood preservative, the concentration of the quaternary ammonium salt composition in the wood preservative is preferably from 0.01 to 80% by mass, more preferably from 0.1 to 60% by mass and still more preferably from 1.0 to 50% by mass.

The configuration of the wood preservative is not particularly limited. The wood preservative may be used in the form of any of an aqueous solution, a wettable powder, a powder, an emulsion, an oil agent and a paste. In this case, depending upon the configuration upon use, the wood preservative may also contain, in addition to the quaternary ammonium salt composition of the present invention, a nonionic surfactant, an anionic surfactant, an amphoteric surfactant, an emulsifier such as high-molecular weight compounds, and a dispersant. Further, one or more kinds of other insecticides or bactericides, mildew-proof agents, etc., may be added to the wood preservative. In addition, the wood preservative may also contain a carrier, a chelating agent, a pH modifier, an antioxidant, a defoaming agent, a pigment, etc., unless the addition thereof adversely affects the effects of the present invention.

The thus produced wood preservative can be used for treating wood by various methods such as a pressure injection method, a vacuum treating method, an immersion method, a spaying method and a coating method to exhibit the effects thereof. Among these methods, the pressure injection method is more preferred for the following reason. That is, in the pressure injection method, the wood preservative is charged into a pressure iron pot together with the wood to be treated, and when applying a pressure thereto, the wood preservative can be penetrated into not only a surface portion of the wood but also a deep inside thereof.

EXAMPLES

In the following examples and comparative examples, "%" represents "% by weight", unless otherwise specified.

Meanwhile, the measurements of mass ratios of the respective components in the quaternary ammonium salt composition and a hue (APHA) and a pH of the quaternary ammonium salt composition, as well as the evaluation of a storage stability of the composition, were conducted by the following methods.

<Method for Measuring Mass Ratios of Respective Components in Quaternary Ammonium Salt Composition (Reaction Mixture)>

The purity (content) of the quaternary ammonium salt in the obtained reaction mixture was determined as follows. That is, the amount of the quaternary ammonium salt contained in the mixture was measured according to the method for quantity determination of dialkyl ($C_{12}$ to $C_{15}$) dimethyl ammonium chloride as prescribed in the standard for materials of quasi-drugs, and the purity of the quaternary ammonium salt in the mixture was calculated from the measured amount in terms of a molecular weight thereof.

The contents of the tertiary amine and the organic acid ester in the obtained reaction mixture as well as the mass ratio of the quaternary ammonium salt of the general formula (1) wherein n is 1 (n=1) to the quaternary ammonium salts of the general formula (1) wherein n is 2 or more (n≧2), were determined as follows. That is, the reaction mixture was subjected to measurement of a proton nuclear magnetic resonance spectrum ($^1$H-NMR), and the contents and the mass ratio were calculated from integral values of signals corresponding to the respective components in the spectrum.

Measuring Device: $^1$H-NMR analyzer "Mercury-400" available from Varian Inc.

Measuring Method: The reaction mixture was dissolved in a mixed solvent containing heavy water and heavy methanol at a mixing volume ratio of 1/1, and the resultant solution was subjected to measurements of the mass ratios of the respective components contained therein by a non-decoupling method.

Measuring Conditions: Concentration: 5%; relaxation time: 3.3 s; pulse: 45°; room temperature; cumulative frequency: 8 times <Method for Measuring Hue (APHA)>

The hue of the resultant raw solution of the quaternary ammonium salt was measured in terms of APHA (according to JIS K0071-1) using a hue meter "OME-2000" (tradename) available from Nippon Denshoku Industries Co., Ltd.

<Method for Measuring pH>

The obtained quaternary ammonium salt was diluted with water to prepare a 1% aqueous solution thereof, and a pH of the obtained aqueous solution was measured at 25° C. using a pH meter "F-52" (tradename) available from HORIBA, Ltd.

<Storage Stability>

The obtained quaternary ammonium salt was subjected to measurements of a hue and a pH thereof by the above methods. Further, the quaternary ammonium salt was preserved at 40° C. for 3 months and then subjected again to the same measurements of the hue and pH thereof. The hue and pH of the quaternary ammonium salt measured before the preservation was compared with those measured after the preservation, and the storage stability of the quaternary ammonium salt was evaluated from the change in hue and pH between before and after the preservation.

Example 1

A 500-mL autoclave equipped with a stirrer and a thermometer was charged with 152.3 g of didecylmethyl amine (0.49 mol), 15.0 g of water (5% on the basis of a total amount (300 g) of the whole components charged), 38.0 g of propionic acid (0.51 mol; 1.05 mol per 1 mol of didecylmethyl amine) and 51.7 g of ethylene glycol (17.2% on the basis of a total amount (300 g) of the whole components charged), and the contents of the autoclave were heated to 65° C. while stirring. Next, 43.1 g of ethyleneoxide (0.98 mol; 2.0 mol per 1 mol of didecylmethyl amine) was charged under pressure into the autoclave, and the contents of the autoclave were aged while stirring for 5 h.

The thus obtained quaternary ammonium salt composition (in the form of a reaction mixture containing the solvents such as water and ethylene glycol) contained the quaternary ammonium salt in an amount of 69.3% (% by mass) in terms of a purity thereof, and the reaction conversion rate to the obtained quaternary ammonium salt was 99%.

Successively, the resultant quaternary ammonium salt was subjected to measurements of a hue and a pH thereof before and after the preservation by the above methods.

Examples 2 to 5 and Comparative Examples 1 to 4

The same procedure as in Example 1 was repeated except for using the conditions shown in Table 1, and the resultant quaternary ammonium salt was subjected to measurements of a hue and a pH thereof before and after the preservation by the above methods. The results are shown in Table 1.

The mass % of water in Comparative Example 1, the molar ratio of the organic acid in Comparative Example 2, the molar ratio of the alkyleneoxide in Comparative Example 3 and the reaction temperature in Comparative Example 4 were respectively controlled to the values out of the specified ranges of the present invention.

TABLE 1

|  | Examples ||||| 
| --- | --- | --- | --- | --- | --- |
|  | 1 | 2 | 3 | 4 | 5 |
| Didecylmethyl amine (g) | 152.3 | 152.3 | 152.3 | 152.3 | 152.3 |
| Water (g) [% based on total mass charged] *1 | 15.0 [5] | 15.0 [5] | 15.0 [5] | 21.0 [7] | 9.0 [3] |
| Propionic acid (g) [molar ratio to amine] *2 | 38.0 [1.05] | 39.8 [1.10] | 43.4 [1.20] | 39.8 [1.10] | 37.3 [1.03] |
| Ethylene glycol (g) [% based on total mass charged] *1 | 51.7 [17.2] | 49.9 [16.6] | 46.2 [15.4] | 33.1 [11.0] | 62.7 [20.9] |
| Ethyleneoxide (g) [molar ratio to amine] *2 | 43.1 [2.0] | 43.1 [2.0] | 43.1 [2.0] | 53.8 [2.5] | 38.7 [1.8] |
| Reaction temperature (° C.)/time (h) | 65/5 | 65/3 | 65/1 | 55/5 | 75/3 |
| Composition of reaction mixture (%) ||||||
| Purity of quaternary salt *3 | 69.3 | 69.4 | 68.6 | 69.4 | 68.8 |
| Tertiary amine [% based on quaternary salt] *4 | 0.5 [0.7] | 0.4 [0.6] | 1.0 [1.5] | 0.4 [0.6] | 0.9 [1.3] |
| Organic acid ester % based on quaternary salt] *4 | 1.2 [1.7] | 2.1 [3.0] | 4.2 [6.0] | 2.1 [3.0] | 1.0 [1.5] |
| Mass ratio (mass %) of quaternary salt (n = 1) to whole quaternary salts *5 | 98 | 99 | 100 | 98 | 99 |
| Reaction conversion rate (%) *6 | 99 | 99 | 98 | 99 | 98 |
| Immediately after production ||||||
| Hue (APHA) | 15 | 20 | 25 | 20 | 40 |
| pH | 7.3 | 7.1 | 6.7 | 6.9 | 7.5 |
| After preserved at 40° C. for 3 months ||||||
| Hue (APHA) | 40 | 40 | 50 | 40 | 50 |
| pH | 6.5 | 6.6 | 6.2 | 6.3 | 6.8 |

|  | Comparative Examples ||||
| --- | --- | --- | --- | --- |
|  | 1 | 2 | 3 | 4 |
| Didecylmethyl amine (g) | 152.3 | 130.5 | 152.3 | 152.3 |
| Water (g) [% based on total mass charged] *1 | 0.2 [0.05] | 15.0 [5] | 15.0 [5] | 15.0 [5] |
| Propionic acid (g) [molar ratio to amine] *2 | 39.8 [1.10] | 49.6 [1.60] | 39.8 [1.10] | 39.8 [1.10] |
| Ethylene glycol (g) [% based on total mass charged] *1 | 64.7 [21.6] | 42.1 [14.0] | 67.1 [22.4] | 49.9 [16.6] |
| Ethyleneoxide (g) [molar ratio to amine] *2 | 43.1 [2.0] | 62.7 [3.4] | 25.8 [1.2] | 43.1 [2.0] |
| Reaction temperature (° C.)/time (h) | 65/3 | 65/3 | 65/5 | 100/3 |
| Composition of reaction mixture (%) |||||
| Purity of quaternary salt *3 | 59.5 | 58.8 | 63.0 | 63.1 |
| Tertiary amine [% based on quaternary salt] *4 | 7.6 [12.8] | 0.9 [1.5] | 5.1 [8.1] | 5.0 [7.9] |
| Organic acid ester % based on quaternary salt] *4 | 4.1 [6.9] | 11.9 [20.2] | 3.8 [6.1] | 3.8 [6.0] |
| Mass ratio (mass %) of quaternary salt (n = 1) to whole quaternary salts *5 | 84 | 89 | 100 | 91 |
| Reaction conversion rate (%) *6 | 85 | 98 | 90 | 90 |

TABLE 1-continued

| | Immediately after production | | | |
|---|---|---|---|---|
| Hue (APHA) | 150 | 70 | 70 | 120 |
| pH | 7.5 | 6.9 | 7.3 | 7.2 |
| | After preserved at 40° C. for 3 months | | | |
| Hue (APHA) | 300 | 250 | 300 | 250 |
| pH | 5.8 | 5.7 | 5.8 | 5.9 |

Note
*[1] Mass % of water or ethylene glycol on the basis of a total mass (g) of the whole components charged
*[2] Molar ratio of propionic acid or ethyleneoxide to didecylmethyl amine (mol)
*[3] Mass % of quaternary ammonium salt in the obtained reaction mixture
*[4] Percentage (%) of tertiary amine or organic acid ester to quaternary ammonium salt
*[5] Percentage (%) of mass of quaternary ammonium salt wherein a molar number of addition of alkyleneoxides is 1 (n = 1) to a total mass of the whole quaternary ammonium salts
*[6] Mol % of the obtained crude product on the basis of didodecylmethyl amine (mol) (assuming that the crude product was made of 100% of the quaternary ammonium salt)

Example 6 to 9

The same procedure as in Example 1 was repeated except that the tertiary amine, the organic acid and the reaction conditions were changed as shown in Table 2, and the resultant quaternary ammonium salt was subjected to measurements of a hue and a pH thereof before and after the preservation by the above methods. The results are shown in Table 2.

TABLE 2

| | Examples | | | |
|---|---|---|---|---|
| | 6 | 7 | 8 | 9 |
| Tertiary amine (g) | Didecylmethyl amine 157.4 | Didecylmethyl amine 151.6 | Didodecylmethyl amine 158.9 | Dimethyloctadecyl amine 150.3 |
| Water (g) [% based on total mass charged] *[7] | 15.0 [5] | 15.0 [5] | 15.0 [5] | 15.0 [5] |
| Organic acid (g) [molar ratio to amine] *[8] | Acetic acid 33.4 [1.10] | Glycolic acid 40.7 [1.10] | Propionic acid 35.2 [1.10] | Propionic acid 41.2 [1.10] |
| Ethylene glycol (g) [% based on total mass charged] *[7] | 67.4 [22.5] | 64.8 [21.6] | 67.8 [22.6] | 64.0 [21.3] |
| Ethyleneoxide (g) [molar ratio to amine] *[8] | 44.5 [2.0] | 42.9 [2.0] | 38.1 [2.0] | 44.5 [2.0] |
| Reaction temperature (° C.)/time (h) | 65/3 | 65/3 | 65/3 | 65/3 |
| Composition of reaction mixture (%) | | | | |
| Purity of quaternary salt *[9] | 69.4 | 68.8 | 68.6 | 69.5 |
| Tertiary amine [% based on quaternary salt] *[10] | 0.4 [0.6] | 0.9 [1.3] | 1.1 [1.5] | 0.4 [0.5] |
| Organic acid ester [% based on quaternary salt] *[10] | 1.9 [2.8] | 2.3 [3.4] | 2.0 [3.0] | 2.2 [3.1] |
| Reaction conversion rate (% based on amine) *[11] | 99 | 99 | 98 | 99 |
| Immediately after production | | | | |
| Hue (APHA) | 20 | 25 | 20 | 15 |
| pH | 7.3 | 6.9 | 7.1 | 7.2 |
| After preserved at 40° C. for 3 months | | | | |
| Hue (APHA) | 30 | 40 | 40 | 30 |
| pH | 6.7 | 6.4 | 6.6 | 6.7 |

Note
*[7] Mass % of water or ethylene glycol on the basis of a total mass (g) of the whole components charged
*[8] Molar ratio of organic acid or ethyleneoxide to tertiary amine (mol)
*[9] Mass % of quaternary ammonium salt in the obtained reaction mixture
*[10] Percentage (%) of tertiary amine or organic acid ester to quaternary ammonium salt
*[11] Mol % of the obtained crude product on the basis of tertiary amine (mol) (assuming that the crude product was composed of 100% of the quaternary ammonium salt)

From Tables 1 and 2, it was confirmed that the compositions obtained in Examples 1 to 9 exhibited a good reaction conversion rate of the amine and a high purity of the quaternary ammonium salt (mass % in the reaction mixture) and were very excellent in hue immediately after the production as compared to the compositions obtained in Comparative Examples 1 to 4. Further, as to the hue and pH of the compositions after the elapse of 3 months, it was confirmed that the compositions obtained in Examples 1 to 9 still exhibited stable hue and pH without deterioration thereof, whereas the compositions obtained in Comparative Examples 1 to 4 suffered from accelerated deterioration especially in hue and, therefore, exhibited a remarkable difference in properties from the quaternary ammonium salt compositions of the present invention.

Thus, in accordance with the present invention, the quaternary ammonium salt exhibiting a good hue and an excellent storage stability can be produced with a high reaction conversion rate.

<Test for Bactericidal Effect of Quaternary Ammonium Salt Composition>

In order to examine properties of the quaternary ammonium salt compositions obtained in Examples 6 to 9 as a wood preservative, the compositions were subjected to the following "Simplified Testing Method for Bactericidal Effect" to evaluate a bactericidal effect thereof on wood-destroying fungi which was required for wood preservatives. The results are shown in Table 3.

In addition, in Comparative Example 5, a quaternary ammonium chloride salt "QUARTAMIN D-10P" (tradename) available from Kao Corp., which was used as the existing wood preservative was subjected to the same testing method for bactericidal effect. The results are shown in Table 3.

Meanwhile, in Table 3, the symbols "−" and "+" mean "−: no growth of fungi occurred" and "+: growth of fungi occurred", respectively.

(Simplified Testing Method for Bactericidal Effect)

The sterilization effect was determined by a minimum growth inhibiting concentration method (MIC method). More specifically, the concentration of a quaternary ammonium salt in the composition was controlled to 50.0 ppm, 10.0 ppm, 5.0 ppm, 2.5 ppm and 1.0 ppm (and 0 ppm) by diluting the composition with water. A sterile water suspension of each of two kinds of fungi, i.e., *Coriolus versicolor* (IFO-30340 strain) and *Tyromyces palustris* (IFO-303339 strain), was inoculated on a PDA culture medium containing the quaternary ammonium salt whose concentration was controlled to the respective concentrations, and the respective fungi were cultured at 25° C. for 10 days to examine whether or not growth of hypha occurred.

TABLE 3

| Wood-destroying fungi tested | Testing concentration (ppm)*12 | Examples | | | | Com. Ex. |
|---|---|---|---|---|---|---|
| | | 6 | 7 | 8 | 9 | 5 |
| *Coriolus versicolor* | 50.0 | − | − | − | − | − |
| | 10.0 | − | − | − | − | − |
| | 5.0 | − | − | − | − | − |
| | 2.5 | + | + | − | − | + |
| | 1.0 | + | + | + | + | + |
| | 0 | + | + | + | + | + |

TABLE 3-continued

| Wood-destroying fungi tested | Testing concentration (ppm)*12 | Examples | | | | Com. Ex. |
|---|---|---|---|---|---|---|
| | | 6 | 7 | 8 | 9 | 5 |
| *Tyromyces palustris* | 50.0 | − | − | − | − | − |
| | 10.0 | − | − | − | − | − |
| | 5.0 | + | + | + | + | + |
| | 2.5 | + | + | + | + | + |
| | 1.0 | + | + | + | + | + |
| | 0 | + | + | + | + | + |

Note
*12Concentration (ppm) of a solution prepared by diluting the quaternary ammonium salt with water From Table 3, it was confirmed that the quaternary ammonium salt produced according to the present invention exhibited an antiseptic effect on wood-destroying fungi which was equal to or greater than that of the existing wood preservatives.

<Test for Bactericidal Effect of Quaternary Ammonium Salt>

The compositions obtained in Examples 1 to 5 and Comparative Examples 1, 2 and 4 as shown in Table 1, were subjected to bactericidal test based on assay of *Escherichia coli*. As a result, it was confirmed that when the comparison in bactericidal effect between the respective compositions was made in terms of a purity of the quaternary ammonium salt, the bactericidal effect of the compositions obtained in Examples 1 to 5 was higher by about 10% than that of the compositions obtained in Comparative Examples 1, 2 and 4.

<Iron Corrosion Test for Quaternary Ammonium Salt Composition>

In order to examine an anti-rusting property against a pressure iron pot used upon treating the wood preservative by a pressure injection method in which the wood preservative was injected under pressure into the pot, the iron corrosiveness of the quaternary ammonium salt compositions obtained in Examples 6 to 9 was evaluated by the following "Simplified Iron Corrosion Testing Method". The results are shown in Table 4.

In Comparative Example 5, there are shown the results of the test conducted using the quaternary ammonium chloride salt "QUARTAMIN D-10P" (tradename) available from Kao Corp., which has been used in the existing wood preservatives.

Meanwhile, in Table 4, the symbols "−" and "+" mean "−: no rust formation occurred" and "+: rust formation occurred", respectively.

<Simplified Iron Corrosion Testing Method>

In the iron corrosion test, a cleaned round iron nail was immersed in a 1% aqueous solution of the quaternary ammonium salt composition to determine formation of rust on the round iron nail with passage of time.

TABLE 4

| | Examples | | | | Com. Ex. |
|---|---|---|---|---|---|
| | 6 (acetic acid)[13] | 7 (glycolic acid)[13] | 8 (propionic acid)[13] | 9 (propionic acid)[13] | 5 (chlorine ion)[13] |
| | Anti-rusting property | | | | |
| 3 h | − | − | − | − | − |
| 10 h | − | − | − | − | + |
| 24 h | − | − | − | − | + |

Note
[13]Terms in parentheses represent counter ions.

From Table 4, it was recognized that the quaternary ammonium salt compositions produced according to the present invention hardly caused rust formation on the surface of the iron nail as compared to the existing wood preservatives. As a result, it was confirmed that the pressure iron pot was free from formation of rust when injecting the wood preservatives under pressure thereinto.

The quaternary ammonium salt composition of the present invention is excellent in hue and storage stability. In accordance with the production process of the present invention, the quaternary ammonium salt composition having excellent hue and storage stability can be produced with a high reaction conversion rate. Further, there can also be provided a wood preservative containing the quaternary ammonium salt composition which exhibits a good antiseptic effect and a good anti-rusting effect.

The invention claimed is:

1. A quaternary ammonium salt composition comprising (a) a quaternary ammonium salt represented by the following general formula (1), (b) a tertiary amine represented by the following general formula (2), and (c) an organic acid ester represented by the following general formula (3), wherein a mass ratio of the component (a) to the component (b) [component (a)/component (b)] is from 100/0.01 to 100/7, and a mass ratio of the component (a) to the component (c) [component (a)/component (c)] is from 100/0.01 to 100/10,

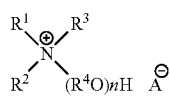  (1)

wherein $R^1$ is an alkyl or alkenyl group having 6 to 24 carbon atoms; $R^2$ is an alkyl, alkenyl or hydroxyalkyl group having 1 to 24 carbon atoms; $R^3$ is an alkyl or hydroxyalkyl group having 1 to 3 carbon atoms; $R^4$ is an alkylene group having 2 to 3 carbon atoms; n is an average molar number of addition of $R^4O$ groups ranging from 1 to 5; and A is a counter ion derived from an organic acid selected from the group consisting of sulfonic acid, a phosphate and a carboxylic acid;

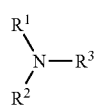  (2)

wherein $R^1$, $R^2$ and $R^3$ have the same meanings as defined above; and $A\text{-}(R^4O)_mH$  (3)

wherein $R^4$ and A have the same meanings as defined above; and m is an average molar number of addition of $R^4O$ groups ranging from 1 to 5.

2. The quaternary ammonium salt composition according to claim 1, wherein in the general formulae (1), (2) and (3), $R^1$ is a linear alkyl group having 8 to 18 carbon atoms; $R^2$ is a methyl group or a linear alkyl group having 8 to 18 carbon atoms; $R^3$ is a methyl group; $R^4$ is an ethylene group; and n is a number of 1 to 1.2.

3. The quaternary ammonium salt composition according to claim 1, wherein a mass (content) of the quaternary ammonium salt represented by the general formula (1) in which n is 1 (n=1), is from 93 to 100% by mass on the basis of a total mass of the whole quaternary ammonium salts contained in the composition.

4. A process for producing the quaternary ammonium salt composition as defined in claim 1 from the tertiary amine (b), comprising the step of reacting the tertiary amine (b) with an alkyleneoxide (e) in the presence of water and an organic acid (d) at a temperature of from 30 to 90° C. wherein the water is present in an amount of from 0.5 to 30% by mass on the basis of the whole components charged, the organic acid (d) is present in an amount of from 0.95 to 1.5 mol per 1 mol of the tertiary amine (b), and the alkyleneoxide (e) is present in an amount of from 1.5 to 5.0 mol per 1 mol of the tertiary amine (b).

5. The process for producing the quaternary ammonium salt composition from the tertiary amine (b) according to claim 4, said process comprising the step of reacting the tertiary amine (b) with the alkyleneoxide (e) in the presence of water and the organic acid (d) at a temperature of from 50 to 78° C. wherein the water is present in an amount of from 1 to 10% by mass on the basis of the whole components charged, the organic acid (d) is present in an amount of from 1.01 to 1.25 mol per 1 mol of the tertiary amine (b), and the alkyleneoxide (e) is present in an amount of from 1.7 to 3.0 mol per 1 mol of the tertiary amine (b).

6. A wood preservative comprising the quaternary ammonium salt composition as defined in claim 1.

* * * * *